United States Patent [19]

Blake et al.

[11] 4,284,833

[45] Aug. 18, 1981

[54] CATALYST REGENERATION

[75] Inventors: Robert J. Blake, Oakland; Guy W. Roy, Richmond, both of Calif.

[73] Assignee: Stauffer Chemical Company, Westport, Conn.

[21] Appl. No.: 862,242

[22] Filed: Dec. 19, 1977

Related U.S. Application Data

[60] Continuation of Ser. No. 697,086, Jun. 16, 1976, abandoned, which is a continuation of Ser. No. 439,455, Feb. 4, 1974, abandoned, which is a continuation of Ser. No. 116,593, Feb. 18, 1971, abandoned, which is a division of Ser. No. 785,389, Dec. 19, 1968, abandoned.

[51] Int. Cl.$^3$ ............................................. C07C 17/152
[52] U.S. Cl. .................................... 570/224; 570/243; 252/411 S
[58] Field of Search .......... 260/654 A, 659 A, 662 A; 570/224, 243

[56] References Cited

U.S. PATENT DOCUMENTS

| | | | |
|---|---|---|---|
| 2,113,028 | 4/1938 | Kuentzel | 252/415 |
| 2,407,701 | 9/1946 | Jones et al. | 252/411 S |
| 3,363,010 | 1/1968 | Schwarzenbek | 260/654 A |
| 3,427,359 | 2/1969 | Rectenwald et al. | 260/659 A |
| 3,440,178 | 4/1969 | Lawrance et al. | 252/415 |
| 3,692,693 | 9/1972 | Gunning et al. | 252/411 S |

*Primary Examiner*—Delbert E. Gantz
*Assistant Examiner*—Joseph A. Boska

[57] ABSTRACT

The active life of an oxychlorination copper-containing catalyst is extended by the removal of sulfur-containing compounds from the gases fed to the catalyst reaction zone. A copper-containing oxychlorination catalyst which has been deactivated by the deposition of sulfur compounds thereon is reactivated in situ by operating the catalyst bed in an oxygen-free atmosphere for a sufficient period of time. The reactivation of the catalyst is completed when the conversions of hydrocarbon and chlorinating agent to chlorinated products indicate a high level of catalyst activity, as determined by an analysis of the gaseous effluent leaving the catalyst bed.

4 Claims, No Drawings

CATALYST REGENERATION

This is a continuation of application Ser. No. 697,086, filed June 16, 1976, now abandoned, which is a continuation of application Ser. No. 439,455, filed Feb. 4, 1974, now abandoned, which is a continuation of application Ser. No. 116,593, filed Feb. 18, 1971, now abandoned, which is a divisional of application Ser. No. 785,389, filed Dec. 19, 1968, now abandoned.

This invention relates to the oxychlorination of hydrocarbons. More particularly, the invention relates to the extension of the active lie and reactivation of copper-containing catalyst compositions, and more specifically to the extension of the active life and reactivation of such catalysts when used in an oxychlorination process.

The oxychlorination of hydrocarbon materials with a chlorinating agent and an oxygen-containing gas is a well known process in the prior art. Suitable known catalysts are employed which accelerate the oxychlorination reaction. The catalysts usually employed comprise the salts, particularly the halides, of metals having variable valences, such as copper chloride. These catalysts are used in both static and fluidized bed oxychlorination reaction zones.

In the oxychlorination art it is well known that an active catalyst is essential to an effective oxychlorination reaction. One of the disadvantages of the copper halide catalyst is that the copper is volatilizable at the required oxychlorination reaction temperatures. Thus, there is a decrease in the active life of the catalyst over an extended period of time due to the loss of the copper halide. This loss has been recognized in the prior art, as shown in U.S. Pat. No. 3,232,889. Copper-containing oxychlorination catalysts are known to be poisoned by impurities entering the oxychlorination reaction zone thereby deactivating the catalyst. In the past, deactivated catalysts were either replaced or reactivated by methods such as controlled oxidation or reduction. Unfortunately, replacement of the catalyst is expensive and can require costly shut down of the process; and prior reactivation methods require additional process equipment and expensive handling procedures.

It is therefore an object of this invention to provide an economical and efficient method for oxychlorination of hydrocarbons.

Another object is to provide an economical and efficient method for the catalytic oxychlorination of hydrocarbons.

Another object is to provide a method for maintaining copper-containing catalytic material in a highly active state over an extended period of operation.

Another object is to provide an in situ reactivation method for deactivated catalysts.

Another object is to provide an effective and economical in situ reactivation method for deactivated copper-containing catalysts used in the oxychlorination of methane.

Another object is to reduce the economic loss suffered through process down time while the catalyst is being replaced or reactivated.

Further objects of this invention will become obvious to one skilled in the art from the detailed description which is contained herein below.

The objects of the present invention are generally accomplished, in accordance with one embodiment of the method of this invention, by maintaining the gaseous material which is fed to a hydrocarbon oxychlorination reaction zone essentially free of sulfur-containing compounds. In the practice of this invention it has been found that the sulfur acts as a promoter in the gases fed to the oxychlorination reaction zone causing the volatilization of the copper component of the oxychlorination catalyst. Accordingly an essentially sulfur-free gaseous feed mixture comprising a hydrocarbon having from 1 to 4 carbon atoms or chlorinated derivatives thereof, an oxygen-containing gas, for example air and oxygen, and a chlorinating agent selected from the group consisting of hydrogen chloride, chlorine and mixtures of chlorine and hydrogen chloride is introduced into an oxychlorination reaction zone containing a suitable copper-containing catalyst. The reaction zone is maintained under oxychlorination reaction conditions to effect the oxychlorination of the feed material to the desired chlorinated hydrocarbon products. It has been found that maintaining the gaseous feed material essentially free of sulfur results in surprising and unexpected extention of catalyst life as will be more fully hereinafter described.

While maintaining an essentially sulfur-free feed results in surprising extention of catalyst life, deposition of sulfur on the catalyst will still occur, thus causing eventual catalyst deactivation.

In another embodiment of this invention, a method is provided for the in situ reactivation of a copper-containing oxychlorination catalyst which has been deactivated by the deposition of sulfur-containing compounds thereon. The method of this embodiment is applicable independent of the level of sulfur-containing impurities in the feed gases to the oxychlorination reaction zone. In accordance with this embodiment, when the deposition of sulfur-containing compounds onto the copper-containing catalyst has deactivated the catalyst to a point where operation is no longer considered economical, the oxygen content of the feed entering the oxychlorination reaction zone is discontinued while maintaining the flow of other constituents of the feed to the oxychlorination reaction zone. It is preferable that the continued flow of the other constituents fed to the reaction zone be sufficient to maintain the catalyst bed in a fluidized state. This discontinuance of the oxygen-containing feed while maintaining the flow of the other feed materials creates an oxygen-free atmosphere in the reaction zone over the catalyst bed. Generally the in situ reactivation method is carried out in an oxychlorination reaction zone maintained between about 350° C. and about 550° C. and a pressure between about zero and about 200 psig. The oxychlorination reaction zone is preferably maintained under operating temperature and pressure, while the flows of hydrocarbon and chlorinating agent continue to the oxychlorination reaction zone during the reactivation period. This procedure is continued for a period of time sufficient to remove deposited sulfur material and reactivate the catalyst.

The term hydrocarbon having from 1 to 4 carbon atoms and chlorinated derivatives thereof includes alkyl, alkenyl, chloroalkyl, and chloroalkenyl such as, e.g., methane, ethane, propane, butane, ethylene, propylene, ethylene dichloride and methyl chloride. This invention will, of course, have application to a wide range of known hydrocarbon oxychlorination processes and therefore this description should not be construed as unduly limiting the scope thereof.

Sulfur-containing compounds which are usually present in the gaseous feed to a hydrocarbon oxychlorination reaction zone are, for example, $H_2S$, $SO_2$, $SO_3$ and the like. The sulfur-containing compounds are present in the hydrocarbon, chlorine or hydrogen chloride as well as oxygen feed streams.

Several known methods are available for removing sulfur-containing compounds from the feed gases and producing essentially sulfur-free gases. These methods include the use of molecular sieves, absorption-stripping zones, carbon absorption and low temperature fractionation.

The term "essentially free of sulfur compounds" as employed herein generally means a feed stream containing less than about 1000 ppm of sulfur. Preferably the sulfur content of the feed material to the oxychlorination zone is less than about 50 ppm and, most preferably, 10 ppm or less of sulfur. At a sulfur level in the oxychlorination feed gases of about five parts per million sulfur the volatilization of copper in the oxychlorination catalyst is minimized while the active life of the oxychlorination catalyst is maximized. At these low levels of sulfur content there is still a deposition of sulfur-containing compounds on the oxychlorination catalyst. The cumulative poisoning effect of the sulfur-containing compounds eventually causes a deactivation of the copper-containing catalyst which then necessitates a reactivation of the catalyst.

Deactivation of the catalyst is considered to take place when the deposition of the sulfur-containing compounds onto the catalyst reaches such a level that an analysis of the gaseous effluent leaving the oxychlorination reaction zone shows that there is a substantial reduction in the percent of the chlorinating agent which is being consumed in the oxychlorination reaction zone.

The continued deposition of sulfur causes the rapid deactivation of the catalyst once the total sulfur content reaches minimum levels in the bed. These levels are between about 2% and about 9% by weight where the sulfur content is expressed as sulfate. It has been found that the sulfur level at which the particular catalyst is deactivated is dependent on the total salt loading of the catalyst.

Reactivation of the copper-containing catalyst is determined by a comparison of the activity of the uncontaminated catalyst when first used in the oxychlorination reaction zone with the activity of the catalyst after it has been subjected to the oxygen-free atmosphere. When these activities are about equal the copper-containing catalyst is considered to have been reactivated.

Deactivation of the catalyst and subsequent reactivation of the catalyst are determined through the analysis of the gaseous effluent leaving the oxychlorination reaction zone. In a methane oxychlorination process, an analysis of the gaseous effluent showing a low percent conversion of hydrogen chloride and a low percent conversion of methane to chlorinated methanes with a high percent oxidation of methane indicates a deactivation of the catalyst. Suitable catalyst reactivation in a methane oxychlorination reaction zone is indicated by an analysis showing a high percent conversion of hydrogen chloride and a high percent conversion of methane to chlorinated methanes with a low percent oxidation of methane. Determination of catalyst deactivation and reactivation can also be based on an analysis of the sulfur content of the catalyst bed. For a particular oxychlorination reaction the deactivation and reactivation of the copper-containing catalyst is dependent on factors such as the lowest percent conversion of reactants to products under which the oxychlorination reaction can be economically operated.

Generally, oxychlorination reaction conditions suitable for use in conjunction with the method of the present invention are well known in the prior art such as the oxychlorination reaction conditions for ethylene as disclosed in U.S. Pat. Nos. 3,173,962, 3,190,931 and 3,210,431 and the oxychlorination reaction conditions for 1,2-dichloroethane as disclosed in U.S. Pat. No. 3,267,160.

In the practice of this invention the operating conditions of a methane oxychlorination reaction zone are of particular interest. A methane oxychlorination reaction zone is operated between about 350° C. and 550° C., and preferably between about 425° C. and 475° C. A methane oxychlorination reaction zone is operated between about zero psig and about 200 psig, and preferably between about zero psig and about 100 psig.

Generally, copper containing catalysts suitable for use in an oxychlorination zone used in conjunction with the method of the present invention are well known in the prior art, such as disclosed in U.S. Pat. Nos. 2,636,864, 3,010,913, 3,210,431 and 3,232,889.

A preferable copper-containing catalyst suitable for use in an oxychlorination reaction zone comprises catalytically effective amounts of a copper halide, an oxidation inhibitor comprising alkali metals such as sodium and potassium and rare earth chlorides and oxides. The rare earth metals have atomic numbers of 57 to 71, the so-called lanthanides. In this specification, in addition to the lanthanides, didymium and yttrium are meant to be included within the term rare earth, Didymium is a commercial designation for a mixture of rare earths.

It has been found that the reactivation method of this invention is advantageously employed in conjunction with a methane oxychlorination process. Accordingly, when it is determined that the copper-containing catalyst used in the methane oxychlorination reaction is deactivated, the present catalyst reactivation method makes it possible to reactivate the catalyst in situ without changing the temperature or pressure in the methane oxychlorination reaction zone. The flow of oxygen to the methane oxychlorination reaction zone is discontinued for a period sufficient to reactivate the catalyst. The discontinuance of the flow of the oxygen-containing feed creates an oxygen-free atmosphere in the oxychlorination reaction zone containing the deactivated catalyst. During reactivation the reaction zone is preferably maintained at a temperature between about 400° C. and about 525° C., most preferably between about 425° C. and about 475° C., and at a pressure preferably between about zero psig and 200 psig and most preferably between about zero psig and about 100 psig. The feed flows of the hydrogen chloride and methane and its chlorinated derivatives are continued during the reactivation period in amounts sufficient to remove the deposited sulforous compounds from the deactivated catalyst. The catalyst activity is restored as the deposited sulfur-containing compounds which poisoned the catalyst leave the catalyst bed during the reactivation period.

When it is determined that the catalyst has been sufficiently reactivated for the requirements of the methane oxychlorination process, oxygen is again fed to the reaction zone together with hydrogen chloride, methane and its chlorinated derivatives.

Having thus described the invention in general terms, reference is now made to the specific examples which should not be construed as unduly limiting thereof.

EXAMPLE I

The catalyst is prepared by mixing 125.1 gms. $CuCl_2.2 H_2O$, 54.7 gms. KCl, 139.2 gms. rare earth oxides, plus 476 gms. water, thereby effecting a 40 weight percent solution of salts. The mixing is done at ambient conditions in a vessel of a size sufficient to contain the components therein.

The solution is then slowly poured onto 1504 gms. of silica-alumina, having a surface area of 1.5-4 m.²/gm. and, a porosity of from about 0.2 to about 0.45 cc./gm. and a particle size of from about 40 to about 150 microns, with mechanical mixing. The moist catalyst is then dried for twenty (20) hours at 140° C.

The dried catalyst is then placed in a Pyrex reactor which consists of a vertical, twenty-inch Pyrex tubular lower portion with an internal diameter of 47 millimeters. the catalyst is supported in the tube by an extra coarse sintered disc which is placed within the tube at the lower end thereof, and contained therein. The bottom of the tube is sealed except for an opening to allow the reaction gases to enter the tube below the sintered disc. The height of the static bed of the catalyst in the tubular section is 10 inches. Attached to the upper end of the tubular portion of the reactor is a tapered section having its broader portion at the upper part thereof, to effect the separation of catalyst fines from the reaction gases. The top portion of the tapered section is adapted with an opening to allow the gaseous effluent to leave the reactor and to allow the insertion of a 10 millimeter outside diameter tube into the catalyst bed extending towards the bottom thereof. The tube has attached thereto, at the lower end thereof, a four-arm spider. The tube and four-arm spider are rotatably mounted. The reactor is electrically heated and it is controlled automatically by means of a thermocouple and a temperature controller.

The salt composition on the catalyst is determined after 110 hours of operation to be 2.4% copper, 1.6% potassium, 6.5% rare earth oxide, and 3.3% $SO_4$. During this time, the operating temperature is 440° C. with a hydrogen chloride rate of 2.81 gram moles per hour, a methane rate of 2.81 gram moles per hour, and an air flow rate of 9.95 gram moles per hour. This results in a superficial velocity of 0.5 feet per second, thereby fluidizing the catalyst. At 265 hours of operation, the catalyst is deactivated as evidenced by a decrease in hydrogen chloride conversion, a decrease in the conversion of methane to chlorinated hydrocarbons and an increase in the amount of methane that is oxidized. The catalyst is then reactivated for one hour at 440° C. During reactivation, the air flow is discontinued but the flow rates of hydrogen chloride and methane are maintained, as well as the temperature and pressure. At the end of this hour, the air is again fed to the reactor and the oxychlorination of the methane is allowed to continue. Table I shows the results of this operation. After reactivation it is seen from Table I that the hydrogen chloride conversion, the conversion of methane to chlorinated hydrocarbons and the methane oxidation catalyst activity values have returned to the levels that the catalyst had initially. It is also seen in Table I that after reactivation there is a significant reduction of the sulfur-containing compounds that remain on the catalyst.

EXAMPLE II

A second catalyst salt loading is prepared using the method Example I sets forth. The catalyst salt composition is set out in Table II. This catalyst is used in a methane oxychlorination reaction zone to which is fed methane, hydrogen chloride and an oxygen-containing gas. The methane oxychlorination reaction conditions are the same as described in Example I. The catalyst of this example is deactivated and reactivated twice during the operation of the methane oxychlorination reaction in the manner as described in Example I. Table II shows the conditions of deactivation and reactivation of the gaseous effluent from the methane oxychlorination reaction zone.

EXAMPLE III

This example illustrates the effect of the sulfur content of the feed mixture to a methane oxychlorination reaction zone which contains a copper-containing catalyst on the rate of volatilization of the copper in the catalyst and on the rate of deactivation of the catalyst.

TABLE I

| HOURS OF OPERATION | % HCl CONVERSION | % CONVERSION TO CHLORINATED METHANES | % CH₄ OXIDIZED | CATALYST COMPOSITION ON AN ALUMINA SUPPORT (Wt. %) | | | |
|---|---|---|---|---|---|---|---|
| | | | | Cu | K | REO* | SO |
| 0 | — | — | — | 2.5 | 1.6 | 6.8 | <0.1 |
| 110 | 90 | 38 | 3.5 | 2.4 | 1.6 | 6.5 | 3.3 |
| 210 | 90 | 38 | 5.5 | 2.2 | 1.6 | 6.3 | 5.8 |
| 265 | 76** | 35 | 16** | 2.0 | 1.6 | 7.2 | 6.8 |
| After Reactivation | 90 | 39 | 3.5 | 2.0 | 1.6 | 3.7 | 0.2 |

*REO = Rare Earth Oxides
** = Considered to be indicative of deactivation

TABLE II

| HOURS OF OPERATION | % HCl CONVERSION | % CH₄ CONVERSION TO CHLORINATED METHANES | % CH₄ OXIDIZED | CATALYST COMPOSITION ON AN ALUMINA SUPPORT (Wt. %) | | | |
|---|---|---|---|---|---|---|---|
| | | | | Cu | K | REO* | SO |
| 0 | — | — | — | 2.7 | 1.8 | 7.9 | <0.1 |
| 220 | 88 | 37 | 4.0 | 1.7 | 1.8 | 7.2 | 6.7 |
| 340 | 54** | 24 | 17.0** | 1.2 | 1.8 | 6.7 | 8.9 |
| After Reactivation | 88 | 39 | 3.5 | | | | |
| 824 | 52** | 28 | 11** | 0.65 | 1.9 | 8.1 | 8.5 |

TABLE II-continued

| HOURS OF OPERATION | % HCl CONVERSION | % CH₄ CONVERSION TO CHLORINATED METHANES | % CH₄ OXIDIZED | CATALYST COMPOSITION ON AN ALUMINA SUPPORT (Wt. %) | | | |
|---|---|---|---|---|---|---|---|
| | | | | Cu | K | REO* | SO |
| After Reactivation | 87 | 38 | 3.0 | | | | |

*REO = Rare Earth Oxides
** = Considered to be indicative of deactivation

In Case I, the average sulfur analysis of the feed gas is approximately 1,800 parts per million sulfur. In Case II, the maximum sulfur content of the feed gas is approximately 40 parts per million sulfur. Table III shows that the high sulfur content feed, Case I, causes a more rapid deactivation of the catalyst and a higher rate of volatilization of the copper from the catalyst than the low sulfur content feed, Case II, causes. These results show that the active life of a copper-containing catalyst usable in a methane oxychlorination reaction zone is extended by use of feed gases having the lowest possible sulfur content.

Having thus described the invention with reference to specific examples thereof, it is to be understood that other modifications, alterations and applications will become apparent to those skilled in the art without departing from the scope of the present invention. Although the method of this invention has been described with reference to oxychlorination reactions, and methane oxychlorination reactions in particular, the method is applicable to copper-containing catalysts that are used in processes outside of the oxychlorination field. In the synthesis of ammonia, it has been found that the copper-containing catalyst is poisoned by oxygen compounds and sulfur-containing compounds. The oxygen compounds do not cause a permanent loss of activity, while the sulfur compounds do. This permanent loss of activity results in a three to five day loss in production, while the catalyst is being reactivated. Using the situ reactivation method herein disclosed, this lost production time can be greatly reduced. The present invention is limited only as defined in the claims appended hereto.

We claim:

1. In a process for the oxychlorination of hydrocarbons in an oxychlorination reaction zone, containing a copper catalyst bed, maintained in a fluidized state at a temperature between about 350° and about 550° C. and a pressure between about zero and about 200 psig wherein a gaseous mixture is fed to said zone, said mixture comprising a hydrocarbon having from 1 to 4 carbon atoms, a chlorinating agent selected from the group consisting of hydrogen chloride, chlorine, or a chlorine-hydrogen chloride mixture, an oxygen-containing gas, said mixture containing less than 1000 ppm of sulfur in the form of sulfur containing compounds such as $H_2S$, $SO_2$ and $SO_3$ which progressively deactivate the catalyst, the improvement which comprises: maintaining the catalyst bed in a fluidized condition while discontinuing the flow of oxygen-containing gas and maintaining the oxychlorination reaction zone at a temperature between about 400° and about 525° C. for a period of time sufficient to remove deposited sulfur material whereby reactivation said catalyst.

2. The process of claim 1 wherein said hydrocarbon is methane.

3. The process of claim 2 wherein the copper containing-catalyst comprises a catalytically effective amount of a copper halide, an oxidation inhibitor selected from the group consisting of potassium and sodium and a rare earth selected from the group consisting of didymium, lanthanum and mixtures of didymium and lanthanum.

4. The process of claim 1 wherein said oxychlorination reaction conditions comprise a temperature between about 425° C. and about 475° C. and a pressure between about zero psig and about 100 psig.

* * * * *

TABLE III

| | Case I | | | | Case II | | | |
|---|---|---|---|---|---|---|---|---|
| TIME (Hrs.) | Start of Run | 240 | 340 Deactivation | 1500 | Start of Run | 240 | 340 | 1500 |
| % HCl Conversion | 88 | 88 | 53 | — | 87 | 87 | 87 | 87 |
| % CH₄ Conversion to Chlorinated Methanes | 37 | 37 | 24 | — | 39 | 39 | 39 | 41 |
| % CH₄ Oxidized | 4 | 4 | 17 | — | 3.8 | 3.8 | 3.8 | 3.8 |
| Salt Analysis | | | | | | | | 1305 hrs. |
| % Cu | 2.5 | — | 1.4 | — | 2.5 | | 2.6 | 2.5 |
| % K | 1.6 | — | 1.6 | — | 1.7 | | 1.8 | 1.7 |
| % SO₄ | 0.04 | — | 8.8 | — | 0.04 | | 0.55 | 0.64 |

UNITED STATES PATENT AND TRADEMARK OFFICE
CERTIFICATE OF CORRECTION

PATENT NO. : 4,284,833
DATED : August 18, 1981
INVENTOR(S) : Robert J. Blake, et al.

It is certified that error appears in the above—identified patent and that said Letters Patent is hereby corrected as shown below:

Column 1, line 13, please change ...lie... to ---life---.

Table I, the heading of the third column should read "% $CH_4$ Conversion to...", instead of "% Conversion...".

Table I, and II, last column please change "SO" to read "$SO_4$".

Column 8, line 30, please change the word "reactivation" to read "reactivating".

Signed and Sealed this

Twentieth Day of October 1981

[SEAL]

Attest:

Attesting Officer

GERALD J. MOSSINGHOFF
Commissioner of Patents and Trademarks